(12) United States Patent
Glaesner et al.

(10) Patent No.: US 7,101,843 B2
(45) Date of Patent: Sep. 5, 2006

(54) GLUCAGON-LIKE PEPTIDE-1 ANALOGS

(75) Inventors: Wolfgang Glaesner, Indianapolis, IN (US); Rohn Lee Millican, Indianapolis, IN (US); Lianshan Zhang, Carmel, IN (US)

(73) Assignee: Eli Lilly and Company, Indianaoplis, IN (US)

( * ) Notice: Subject to any disclaimer, the term of this patent is extended or adjusted under 35 U.S.C. 154(b) by 0 days.

(21) Appl. No.: 10/485,619

(22) PCT Filed: Aug. 14, 2002

(86) PCT No.: PCT/US02/21325

§ 371 (c)(1),
(2), (4) Date: Jan. 29, 2004

(87) PCT Pub. No.: WO03/018516

PCT Pub. Date: Mar. 6, 2003

(65) Prior Publication Data

US 2004/0198654 A1    Oct. 7, 2004

Related U.S. Application Data

(60) Provisional application No. 60/314,573, filed on Aug. 23, 2001.

(51) Int. Cl.
*A61K 38/26* (2006.01)
*C07K 14/605* (2006.01)

(52) U.S. Cl. ............................. 514/2; 514/12; 530/308; 530/324

(58) Field of Classification Search ................ 530/308; 514/2
See application file for complete search history.

(56) References Cited

U.S. PATENT DOCUMENTS 5,545,618 A    8/1996   Buckley et al.

FOREIGN PATENT DOCUMENTS

| EP | 0926159 | * | 6/1999 |
|---|---|---|---|
| WO | WO 91/11457 | | 8/1991 |
| WO | WO 98/19698 | * | 5/1998 |
| WO | WO 99/30731 A | | 6/1999 |
| WO | WO 99/43341 | | 9/1999 |
| WO | WO 99/43706 | | 9/1999 |
| WO | WO 00/07617 | | 2/2000 |
| WO | WO 00/55119 A | | 9/2000 |
| WO | WO 01/98331 | | 12/2001 |

* cited by examiner

*Primary Examiner*—Anish Gupta
(74) *Attorney, Agent, or Firm*—Gregory A. Cox (57) ABSTRACT

Disclosed are glucagon-like peptide-1 (GLP-1) compounds with modifications at one or more of the following positions: 7, 8, 12, 16, 18, 19, 20, 22, 25, 27, 30, 33, and 37. Methods of treating a subject in need of GLP-1 receptor stimulation using these GLP-1 compounds are also disclosed.

5 Claims, 3 Drawing Sheets

Figure 1   Plasma insulin levels during IVGTT after administration of V8GLP G22E A25V V33I at different doses

Fig. 3

GLUCAGON-LIKE PEPTIDE-1 ANALOGS

This is the national phase application, under 35 USC 371, for PCT/US02/21325, filed Aug. 14, 2002, which claims the priority of U.S. provisional application No. 60/314,573, filed Aug. 23, 2001.

Over the past several decades, continuous strides have been made to improve the treatment of diabetes mellitus. Approximately 90% of people with diabetes have type 2 diabetes also known as non-insulin dependent diabetes mellitus (NIDDM). Type 2 diabetics generally still make insulin, but the insulin cannot be used effectively by the body's cells. This is primarily because the amount of insulin produced in response to rising blood sugar levels is not sufficient to allow cells to efficiently take up glucose and thus, reduce blood sugar levels.

Often, individuals with NIDDM can initially control their blood glucose levels by taking oral medications. However, oral medications do not slow the progressive loss of β cell function that occurs in type 2 patients and eventually these types of medications are not sufficient to control blood glucose levels.

A large body of pre-clinical and clinical research data suggests that glucagon-like pepide-1 (GLP-1) shows great promise as a treatment for NIDDM especially when oral agents begin to fail. GLP-1 induces numerous biological effects such as stimulating insulin secretion, inhibiting glucagon secretion, inhibiting gastric emptying, enhancing glucose utilization, and inducing weight loss. Further, pre-clinical studies suggest that GLP-1 may also act to prevent the β cell deterioration that occurs as the disease progresses. Perhaps the most salient characteristic of GLP-1 is its ability to stimulate insulin secretion without the associated risk of hypoglycemia that is seen when using insulin therapy or some types of oral therapies that act by increasing insulin expression.

As NIDDM progresses it becomes extremely important to achieve near normal glycemic control and thereby minimize the complications associated with prolonged hyperglycemia. GLP-1 would appear to be the drug of choice. However, the usefulness of therapy involving GLP-1 peptides has been limited by the fact that GLP-1(1–37) is poorly active, and the two naturally occurring truncated peptides, GLP-1(7–37) OH and GLP-1(7–36)NH$_2$, are rapidly cleared in vivo and have extremely short in vivo half-lives. Further, GLP-1 compound formulations currently in development cannot be given orally and like insulin must be injected. Thus, despite the clear medical advantages associated with therapy involving GLP-1, the short half-life which results in a drug that must be injected one or more times a day has impeded commercial development efforts.

Generally, moving patients to an injectable therapy is quite difficult. Many diabetics are unwilling to undertake any type of intensive injection therapy due to the discomfort associated with the many injections required to maintain adequate glucose control. Furthermore, diabetics on insulin are generally required to monitor their blood glucose which involves additional needle sticks. This type of therapy can be both psychologically and physically painful. This is especially true when patients have been treated solely with oral medications throughout the progression of the disease. Thus, there is a need for a non-injectable therapy that involves administration of a GLP-1 compound by alternative means such as by the oral or pulmonary route. Non-invasive delivery technology provides a means to increase patient convenience and hence compliance with a therapy that could potentially delay the onset of type-2 diabetes. GLP-1 analogs that have been previously described do not lend themselves to this technology because their potency is generally too low to offset the anticipated drop in bioavailability associated with administration by the oral or pulmonary route compared to a subcutaneous injection. Thus, a limiting factor with respect to oral or pulmonary administration of proteins and peptides is the relatively large amount of protein required due to poor absorption and local metabolism.

The present invention solves the problems associated with non-invasive delivery of GLP-1 through the development of novel GLP-1 analogs that are extremely potent. The increased potency of these analogs facilitates the use of delivery technology associated with limited bioavailability. The present invention makes possible non-injectable therapy through the delivery of cost-effective amounts of a potent biologically active GLP-1 compound such that therapeutic serum levels are achieved.

It has now been found that a number of GLP-1 compounds with modifications at one or more of the following positions: 8, 12, 16, 18, 19, 20, 22, 25, 27, 30, 33, and 37 show increased potency compared with Val$^8$-GLP-1(7–37) OH.

One embodiment of the present invention is a GLP-1 compound comprising the amino acid sequence of formula 1 (SEQ ID NO:1)

```
Xaa7-Xaa8-Glu-Gly-Thr-Xaa12-Thr-Ser-Asp-Xaa16-Ser-    Formula 1 (SEQ ID NO: 1)

Xaa18-Xaa19-Xaa20-Glu-Xaa22-Gln-Ala-Xaa25-Lys -Xaa27-

Phe-Ile-Xaa30-Trp-Leu-Xaa33-Lys-Gly-Arg-Xaa37
``` wherein:
Xaa$_7$ is: L-histidine, D-histidine, desamino-histidine, 2-amino-histidine, β-hydroxy-histidine, homohistidine, α-fluoromethyl-histidine, or α-methyl-histidine;
Xaa$_8$ is: Ala, Gly, Val, Leu, Ile, Ser, or Thr;
Xaa$_{12}$ is: Phe, Trp, or Tyr;
Xaa$_{16}$ is: Val, Trp, Ile, Leu, Phe, or Tyr;
Xaa$_{18}$ is: Ser, Trp, Tyr, Phe, Lys, Ile, Leu, or Val;
Xaa$_{19}$ is: Tyr, Trp, or Phe;
Xaa$_{20}$ is: Leu, Phe, Tyr, or Trp;
Xaa$_{22}$ is: Gly, Glu, Asp, or Lys;
Xaa$_{25}$ is: Ala, Val, Ile, or Leu;
Xaa$_{27}$ is: Glu, Ile, or Ala;
Xaa$_{30}$ is: Ala or Glu
Xaa$_{33}$ is: Val, or Ile; and
Xaa$_{37}$ is: Gly, His, NH$_2$, or is absent.

provided that the GLP-1 compound does not have the sequence of GLP-1(7–37)OH, GLP-1(7–36)-NH$_2$, Gly$^8$-GLP-1(7–37)OH, Gly$^8$-GLP-1(7–36)NH$_2$, Val$^8$-GLP-1(7–37)OH, Val$^8$-GLP-1(7–36)NH$_2$, Lue$^8$-GLP-1(7–37)OH, Leu$^8$-GLP-1(7–36)NH$_2$, Ile$^8$-GLP-1(7–37)OH, Ile$^8$-GLP-1(7–36)NH$_2$, Ser$^8$-GLP-1(7–37)OH, Ser$^8$-GLP-1(7–36)NH$_2$, Thr⁸-GLP-1(7–37)OH, Thr⁸-GLP-1(7–36)NH₂, Val⁸-Tyr¹²-GLP-1(7–37)OH, Val⁸-Tyr¹²-GLP-1(7–36)NH₂, Val⁸-Tyr¹⁶-GLP-1(7–37)OH, Val⁸-Tyr¹⁶-GLP-1(7–36)NH₂, Val⁸-Glu²²-GLP-1(7–37)OH, Val⁸-Glu²²-GLP-1(7–36)NH₂, Gly⁸-Glu²²-GLP-1(7–37)OH, Gly⁸-Glu²²-GLP-1(7–36)NH₂, Val⁸-Asp²²-GLP-1(7–37)OH, Val⁸-Asp²²-GLP-1(7–36)NH₂, Gly⁸-Asp²²-GLP-1(7–37)OH, Gly⁸-Asp²²-GLP-1(7–36)NH₂, Val⁸-Lys²²-GLP-1(7–37)OH, Val⁸-Lys²²-GLP-1(7–36)NH₂, Gly⁸-Lys²²-GLP-1(7–37)OH, Gly⁸-Lys²²-GLP-1(7–36)NH₂, Leu⁸-Glu²²-GLP-1(7–37)OH, Leu⁸-Glu²²-GLP-1(7–36)NH₂, Ile⁸-Glu²²-GLP-1(7–37)OH, Ile⁸-Glu²²-GLP-1(7–36)NH₂, Leu⁸-Asp²²-GLP-1(7–37)OH, Leu⁸-Asp²²-GLP-1(7–36)NH₂, Ile⁸-Asp²²-GLP-1(7–37)OH, Ile⁸-Asp²²-GLP-1(7–36)NH₂, Leu⁸-Lys²²-GLP-1(7–37)OH, Leu⁸-Lys²²-GLP-1(7–36)NH₂, Ile⁸-Lys²²-GLP-1(7–37)OH, Ile⁸-Lys²²-GLP-1(7–36)NH₂, Ser⁸-Glu²²-GLP-1(7–37)OH, Ser⁸-Glu²²-GLP-1(7–36)NH₂, Thr⁸-Glu²²-GLP-1(7–37)OH, Thr⁸-Glu²²-GLP-1(7–36)NH₂, Ser⁸-Asp²²-GLP-1(7–37)OH, Ser⁸-Asp²²-GLP-1(7–36)NH₂, Thr⁸-Asp²²-GLP-1(7–37)OH, Thr⁸-Asp²²-GLP-1(7–36)NH₂, Ser⁸-Lys²²-GLP-1(7–37)OH, Ser⁸-Lys²²-GLP-1(7–36)NH₂, Thr⁸-Lys²²-GLP-1(7–37)OH, Thr⁸-Lys²²-GLP-1(7–36)NH₂, Glu²²-GLP-1(7–37)OH, Glu²²-GLP-1(7–36)NH₂, Asp²²-GLP-1(7–37)OH, Asp²²-GLP-1(7–36)NH₂, Lys²²-GLP-1(7–37)OH, Lys²²-GLP-1(7–36)NH₂, Val⁸-Ala²⁷-GLP-1(7–37)OH, Val⁸-Glu²²-Ala²⁷-GLP-1(7–37)OH, Val⁸-Glu³⁰-GLP-1(7–37)OH, Val⁸-Glu³⁰-GLP-1(7–36)NH₂, Gly⁸-Glu³⁰-GLP-1(7–37)OH, Gly⁸-Glu³⁰-GLP-1(7–36)NH₂, Leu⁸-Glu³⁰-GLP-1(7–37)OH, Leu⁸-Glu³⁰-GLP-1(7–36)NH₂, Ile⁸-Glu³⁰-GLP-1(7–37)OH, Ile⁸-Glu³⁰-GLP-1(7–36)NH₂, Ser⁸-Glu³⁰-GLP-1(7–37)OH, Ser⁸-Glu³⁰-GLP-1(7–36)NH₂, Thr⁸-Glu³⁰-GLP-1(7–37)OH, Thr⁸-Glu³⁰-GLP-1(7–36)NH₂, Val⁸-His³⁷-GLP-1(7–37)OH, Val⁸-His³⁷-GLP-1(7–36)NH₂, Gly⁸-His³⁷-GLP-1(7–37)OH, Gly⁸-His³⁷-GLP-1(7–36)NH₂, Leu⁸-His³⁷-GLP-1(7–37)OH, Leu⁸-His³⁷-GLP-1(7–36)NH₂, Ile⁸-His³⁷-GLP-1(7–37)OH, Ile⁸-His³⁷-GLP-1(7–36)NH₂, Ser⁸-His³⁷-GLP-1(7–37)OH, Ser⁸-His³⁷-GLP-1(7–36)NH₂, Thr⁸-His³⁷-GLP-1(7–37)OH, Thr⁸-His³⁷-GLP-1(7–36)NH₂.

Another embodiment of the present invention is a GLP-1 compound comprising the amino acid sequence of formula II (SEQ ID NO:2):

```
Xaa₇-Xaa₈-Glu-Gly-Thr-Phe-Thr-Ser-Asp-Xaa₁₆-Ser-          Formula II (SEQ ID NO: 2)

Xaa₁₈-Tyr-Leu-Glu-Xaa₂₂-Gln-Ala-Xaa₂₅-Lys-Glu-Phe-

Ile-Ala-Trp-Leu-Xaa₃₃-Lys-Gly-Arg-Xaa₃₇
``` wherein:
Xaa₇ is: L-histidine, D-histidine, desamino-histidine, 2-amino-histidine, β-hydroxy-histidine, homohistidine, α-fluoromethyl-histidine, or α-methyl-histidine;
Xaa₈ is: Gly, Ala, Val, Leu, Ile, Ser, or Thr;
Xaa₁₆ is: Val, Phe, Tyr, or Trp;
Xaa₁₈ is: Ser, Tyr, Trp, Phe, Lys, Ile, Leu, or Val;
Xaa₂₂ is: Gly, Glu, Asp, or Lys;
Xaa₂₅ is: Ala, Val, Ile, or Leu;
Xaa₃₃ is: Val or Ile; and
Xaa₃₇ is: Gly, NH₂, or is absent.

provided that the GLP-1 compound does not have the sequence of GLP-1(7–37)OH, GLP-1(7–36)-NH₂, Gly⁸-GLP-1(7–37)OH, Gly⁸-GLP-1(7–36)NH₂, Val⁸-GLP-1(7–37)OH, Val⁸-GLP-1(7–36)NH₂, Lue⁸-GLP-1(7–37)OH, Leu⁸-GLP-1(7–36)NH₂, Ile⁸-GLP-1(7–37)OH, Ile⁸-GLP-1(7–36)NH₂, Ser⁸-GLP-1(7–37)OH, Ser⁸-GLP-1(7–36)NH₂, Thr⁸-GLP-1(7–37)OH, Thr⁸-GLP-1(7–36)NH₂, Val⁸-Tyr¹⁶-GLP-1(7–37)OH, Val⁸-Tyr¹⁶-GLP-1(7–36)NH₂, Val⁸-Glu²²-GLP-1(7–37)OH, Val⁸-Glu²²-GLP-1(7–36)NH₂, Gly⁸-Glu²²-GLP-1(7–37)OH, Gly⁸-Glu²²-GLP-1(7–36)NH₂, Val⁸-Asp²²-GLP-1(7–37)OH, Val⁸-Asp²²-GLP-1(7–36)NH₂, Gly⁸-Asp²²-GLP-1(7–37)OH, Gly₈-Asp²²-GLP-1(7–36)NH₂, Val⁸-Lys²²-GLP-1(7–37)OH, Val⁸-Lys²²-GLP-1(7–36)NH₂, Gly⁸-Lys²²-GLP-1(7–37)OH, Gly⁸-Lys²²-GLP-1(7–36)NH₂, Leu⁸-Glu²²-GLP-1(7–37)OH, Leu⁸-Glu²²-GLP-1(7–36)NH₂, Ile⁸-Glu²²-GLP-1(7–37)OH, Ile⁸-Glu²²-GLP-1(7–36)NH₂, Leu⁸-Asp²²-GLP1(7–37)OH, Leu⁸-Asp²²-GLP-1(7–36)NH₂, Ile⁸-Asp²²-GLP-1(7–37)OH, Ile⁸-Asp²²-GLP-1(7–36)NH₂, Leu⁸-Lys²²-GLP-1(7–37)OH, Leu⁸-Lys²²-GLP-1(7–36)NH₂, Ile⁸-Lys²²-GLP-1(7–37)OH, Ile⁸-Lys²²-GLP-1(7–36)NH₂, Ser⁸-Glu²²-GLP-1(7–37)OH, Ser⁸-Glu²²-GLP-1(7–36)NH₂, Thr⁸-Glu²²-GLP-1(7–37)OH, Thr⁸-Glu²²-GLP-1(7–36)NH₂, Ser₈-Asp²²-GLP-1(7–37)OH, Ser⁸-Asp²²-GLP-1(7–36)NH₂, Thr⁸-Asp²²-GLP-1(7–37)OH, Thr⁸-Asp²²-GLP-1(7–36)NH₂, Ser⁸-Lys²²-GLP-1(7–37)OH, Ser⁸-Lys²²-GLP-1(7–36)NH₂, Thr⁸-Lys²²-GLP-1(7–37)OH, Thr⁸-Lys²²-GLP-1(7–36)NH₂, Glu²²-GLP-1(7–37)OH, Glu²²-GLP-1(7–36)NH₂, Asp²²-GLP-1(7–37)OH, Asp²²-GLP-1(7–36)NH₂, Lys²²-GLP-1(7–37)OH, Lys²²-GLP-1(7–36)NH₂.

Preferred embodiments of formula I and II include GLP-1 compounds that do not differ from GLP-1(7–37)OH or GLP-1(7–36)NH₂ by more than 6 amino acids, by more than 5 amino acids, by more than 4 amino acids, or by more than 3 amino acids. It is also preferable that the GLP-1 compounds of formula I and II have valine or glycine at position 8 and glutamic acid at position 22. It is also preferable that the GLP-1 compounds of formula I and II have valine or glycine at position 8 and glutamic acid at position 30. It is also preferable that the GLP-1 compounds of formula I and II have valine or glycine at position 8 and histidine at position 37.

The present invention also encompasses a method of stimulating the GLP-1 receptor in a subject in need of such stimulation, said method comprising the step of administering to the subject an effective amount of the GLP-1 compounds described herein. Subjects in need of GLP-1 receptor stimulation include those with non-insulin dependent diabetes and obesity FIG. 1 graphs plasma insulin and plasma glucose concentrations obtained at various time points after injection of increasing concentrations of Val⁸-GLP-1(7–37)OH in rats.

A GLP-1 compound is a polypeptide having from about twenty-five to about thirty-nine naturally occurring or non-naturally occurring amino acids and has sufficient homology to GLP-1(7–37)OH such that it exhibits insulinotropic activity.

"Insulinotropic activity" refers to the ability to stimulate insulin secretion in response to elevated glucose levels, thereby causing glucose uptake by cells and decreased plasma glucose levels. Insulinotropic activity can be assessed by methods known in the art, including using in vivo experiments and in vitro assays that measure GLP-1 receptor binding activity or receptor activation, e.g., assays employing pancreatic islet cells or insulinoma cells, as described in EP 619,322 to Gelfand, et al., and U.S. Pat. No. 5,120,712, respectively. The entire teachings of these references are incorporated herein by reference. Insulinotropic activity is routinely measured in humans by measuring insulin levels or C-peptide levels.

Examples of non-naturally occurring amino acids include α-methyl amino acids (e.g., α-methyl alanine), D-amino acids, histidine-like amino acids (e.g., 2-amino-histidine, β-hydroxy-histidine, homohistidine, (α-fluoromethyl-histidine and α-methyl-histidine), amino acids having an extra methylene in the side chain ("homo"amino acids) and amino acids in which a carboxylic acid functional group in the side chain is replaced with a sulfonic acid group (e.g., cysteic acid). Preferably, however, the GLP-1 compounds of the present invention comprise only naturally occurring amino acids except as otherwise specifically provided herein.

A GLP-1 compound typically comprises a polypeptide having the amino acid sequence of GLP-1(7–37)OH, an analog of GLP-1(7–37)OH, a fragment of GLP-1(7–37)OH or a fragment of a GLP-1(7–37)OH analog. GLP-1(7–37)OH has the amino acid sequence of SEQ ID NO: 3:

```
⁷His-Ala-Glu-¹⁰Gly-Thr-Phe-Thr-Ser-¹⁵Asp-Val-Ser-Ser-    (SEQ ID NO: 3)
Tyr-²⁰Leu-Glu-Gly-Gln-Ala-²⁵Ala-Lys-Glu-Phe-Ile-³⁰Ala-
Trp-Leu-Val-Lys-³⁵Gly-Arg-³⁷Gly
```

By custom in the art, the amino terminus of GLP-1(7–37)OH has been assigned number residue 7 and the carboxy-terminus, number 37. The other amino acids in the polypeptide are numbered consecutively, as shown in SEQ ID NO: 3. For example, position 12 is phenylalanine and position 22 is glycine. When not specified, the C-terminal is in the traditional carboxyl form.

A "GLP-1 fragment" is a polypeptide obtained after truncation of one or more amino acids from the N-terminus and/or C-terminus of GLP-1(7–37)OH or a GLP-1(7–37)OH analog. The nomenclature used to describe GLP-1(7–37)OH carries over to GLP-1 fragments. For example, GLP-1(9–36)OH denotes a GLP-1 fragment obtained by truncating two amino acids from the N-terminus and one amino acid from the C-terminus. The amino acids in the fragment are denoted by the same number as the corresponding amino acid in GLP-1(7–37)OH. For example, the N-terminal glutamic acid in GLP-1(9–36)OH is at position 9; position 12 is occupied by phenylalanine; and position 22 is occupied by glycine, as in GLP-1(7–37)OH.

GLP-1 compounds include "GLP-1 analogs" which have sufficient homology to GLP-1(7–37)OH, GLP-1(7–36)NH₂ or a fragment of GLP-1(7–37)OH or GLP-1(7–36)NH₂ such that the analog has insulinotropic activity. Preferably, a GLP-1 analog has the amino acid sequence of GLP-1(7–37)OH or a fragment thereof, modified so that from one, two, three, four, five, or six amino acids differ from the amino acid in the corresponding position of GLP-1(7–37)OH or a fragment of GLP-1(7–37)OH. In the nonmenclature used herein to designate GLP-1 compounds, the substituting amino acid and its position is indicated prior to the parent structure. For example, Glu²²-GLP-1(7–37)OH designates a GLP-1 compound in which the glycine normally found at position 22 of GLP-1(7–37)OH has been replaced with glutamic acid; Val⁸-Glu²²-GLP-1(7–37)OH designates a GLP-1 compound in which alanine normally found at position 8 and glycine normally found at position 22 of GLP-1(7–37)OH have been replaced with valine and glutamic acid, respectively.

The GLP-1 compounds of the present invention have increased potency compared to Val⁸-GLP-1(7–37)OH. Native GLP-1(7–37)OH is rapidly degraded by dipeptidy-lamino-peptidase IV (DPP-IV) after injection and the half-life of GLP-1(7–37)OH is approximately five minutes. Analogs such as Val⁸-GLP-1(7–37)OH wherein the alanine at position 8 has been substituted with a different amino acid have been developed because these analogs are resistant to DPP-IV degradation and thus, have an increased half-life. However, these analogs are generally not potent enough to make administration by alternative delivery technology feasible on a commercial scale. Thus, Val⁸-GLP-1(7–37)OH is used as a comparator to illustrate the increased potency of the novel GLP-1 compounds encompassed by the present invention.

Preferably, the GLP-1 compounds of the present invention comprise GLP-1 analogs wherein the backbone for such analogs or fragments contains an amino acid other than alanine at position 8 (position 8 analogs). The backbone may also include L-histidine, D-histidine, or modified forms of histidine such as desamino-histidine, 2-amino-histidine, β-hydroxy-histidine, homohistidine, α-fluoromethyl-histidine, or α-methyl-histidine at position 7. It is preferable that these position 8 analogs contain one or more additional changes at positions 12, 16, 18, 19, 20, 22, 25, 27, 30, 33, and 37 compared to the corresponding amino acid of native GLP-1(7–37)OH. It is more preferable that these position 8 analogs contain one or more additional changes at positions 16, 18, 22, 25 and 33 compared to the corresponding amino acid of native GLP-1(7–37)OH.

In a preferred embodiment, the GLP-1 analog is GLP-1(7–37)OH wherein the amino acid at position 12 is selected the group consisting of tryptophan or tyrosine. It is more preferred that in addition to the substitution at position 12, the amino acid at position 8 is substituted with glycine, valine, leucine, isoleucine, serine, threonine, or methionine and more preferably valine or glycine. It is even more preferred that in addition to the substitutions at position 12 and 8, the amino acid at position 22 is substituted with glutamic acid.

In another preferred embodiment, the GLP-1 analog is GLP-1(7–37)OH wherein the amino acid at position 16 is selected from the group consisting of tryptophan, isoleucine, leucine, phenylalanine, or tyrosine. It is more preferred that in addition to the substitution at position 16, the amino acid at position B is substituted with glycine, valine, leucine, isoleucine, serine, threonine, or methionine and more preferably valine or glycine. It is even more preferred that in addition to the substitutions at position 16 and 8, the amino acid at position 22 is substituted with glutamic acid. It is also preferred that in addition to the substitutions at positions 16 and 8, the amino acid at position 30 is substituted with glutamic acid. It is also preferred that in addition to the substitutions at positions 16 and 8, the amino acid at position 37 is substituted with histidine.

In another preferred embodiment, the GLP-1 analog is GLP-1(7–37)OH wherein the amino acid at position 18 is selected from the group consisting of tryptophan, tyrosine, phenylalanine, lysine, leucine, or isoleucine, preferably tryptophan, tyrosine, and isoleucine. It is more preferred that in addition to the substitution at position 18, the amino acid at position 8 is substituted with glycine, valine, leucine, isoleucine, serine, threonine, or methionine and more preferably valine or glycine. It is even more preferred that in addition to the substitutions at position 18 and 8, the amino acid at position 22 is substituted with glutamic acid. It is also preferred that in addition to the substitutions at positions 18 and 8, the amino acid at position 30 is substituted with glutamic acid. It is also preferred that in addition to the substitutions at positions 18 and 8, the amino acid at position 37 is substituted with histidine In another preferred embodiment, the GLP-1 analog is GLP-1(7–37)OH wherein the amino acid at position 19 is selected from the group consisting of tryptophan or phenylalanine, preferably tryptophan. It is more preferred that in addition to the substitution at position 19, the amino acid at position 8 is substituted with glycine, valine, leucine, isoleucine, serine, threonine, or methionine and more preferably valine or glycine. It is even more preferred that in addition to the substitutions at position 19 and 8, the amino acid at position 22 is substituted with glutamic acid. It is also preferred that in addition to the substitutions at positions 19 and 8, the amino acid at position 30 is substituted with glutamic acid. It is also preferred that in addition to the substitutions at positions 19 and 8, the amino acid at position 37 is substituted with histidine

In another preferred embodiment, the GLP-1 analog is GLP-1(7–37)OH wherein the amino acid at position 20 is phenylalanine, tyrosine, or tryptophan. It is more preferred that in addition to the substitution at position 20, the amino acid at position 8 is substituted with glycine, valine, leucine, isoleucine, serine, threonine, or methionine and more preferably valine or glycine. It is even more preferred that in addition to the substitutions at position 20 and 8, the amino acid at position 22 is substituted with glutamic acid. It is also preferred that in addition to the substitutions at positions 20 and 8, the amino acid at position 30 is substituted with glutamic acid. It is also preferred that in addition to the substitutions at positions 20 and 8, the amino acid at position 37 is substituted with histidine In another preferred embodiment, the GLP-1 analog is GLP-1(7–37)OH wherein the amino acid at position 25 is selected from the group consisting of valine, isoleucine, and leucine, preferably valine. It is more preferred that in addition to the substitution at position 25, the amino acid at position 8 is substituted with glycine, valine, leucine, isoleucine, serine, threonine, or methionine and more preferably valine or glycine. It is even more preferred that in addition to the substitutions at position 25 and 8, the amino acid at position 22 is substituted with glutamic acid. It is also preferred that in addition to the substitutions at positions 25 and 8, the amino acid at position 30 is substituted with glutamic acid. It is also preferred that in addition to the substitutions at positions 25 and 8, the amino acid at position 37 is substituted with histidine.

In another preferred embodiment, the GLP-1 analog is GLP-1(7–37)OH wherein the amino acid at position 27 is selected from the group consisting of isoleucine or alanine. It is more preferred that in addition to the substitution at position 27, the amino acid at position 8 is substituted with glycine, valine, leucine, isoleucine, serine, threonine, or methionine and more preferably valine or glycine. It is even more preferred that in addition to the substitutions at position 27 and 8, the amino acid at position 22 is substituted with glutamic acid. It is also preferred that in addition to the substitutions at positions 27 and 8, the amino acid at position 30 is substituted with glutamic acid. It is also preferred that in addition to the substitutions at positions 27 and 8, the amino acid at position 37 is substituted with histidine In another preferred embodiment, the GLP-1 analog is GLP-1(7–37)OH wherein the amino acid at position 33 is isoleucine. It is more preferred that in addition to the substitution at position 33, the amino acid at position 8 is substituted with glycine, valine, leucine, isoleucine, serine, threonine, or methionine and more preferably valine or glycine. It is even more preferred that in addition to the substitutions at position 33 and 8, the amino acid at position 22 is substituted with glutamic acid. It is also preferred that in addition to the substitutions at positions 33 and 8, the amino acid at position 30 is substituted with glutamic acid. It is also preferred that in addition to the substitutions at positions 33 and 8, the amino acid at position 37 is substituted with histidine It is also preferable that the GLP-1 compounds of the present invention have other combinations of substituted amino acids. The present invention encompasses a GLP-1 compound comprising the amino acid sequence of formula 1 (SEQ ID NO:1)

Formula 1 (SEQ ID NO: 1)

wherein:
Xaa$_7$ is: L-histidine, D-histidine, desamino-histidine, 2-amino-histidine, β-hydroxy-histidine, homohistidine, α-fluoromethyl-histidine, or α-methyl-histidine;
Xaa$_8$ is: Ala, Gly, Val, Leu, Ile, Ser, or Thr;
Xaa$_{12}$ is: Phe, Trp, or Tyr;
Xaa$_{16}$ is: Val, Trp, Ile, Leu, Phe, or Tyr;
Xaa$_{18}$ is: Ser, Trp, Tyr, Phe, Lys, Ile, Leu, or Val;
Xaa$_{19}$ is: Tyr, Trp, or Phe;
Xaa$_{20}$ is: Leu, Phe, Tyr, or Trp;
Xaa$_{22}$ is: Gly, Glu, Asp, Lys;
Xaa$_{25}$ is: Ala, Val, Ile, or Leu;
Xaa$_{27}$ is: Glu, Ile, or Ala;
Xaa$_{30}$ is: Ala or Glu
Xaa$_{33}$ is: Val, or Ile; and Xaa$_{37}$ is: Gly, His, NH$_2$, or is absent.

provided that the GLP-1 compound does not have the sequence of GLP-1(7–37)OH, GLP-1(7–36)-NH$_2$, Gly$^8$-GLP-1(7–37)OH, Gly$^8$-GLP-1(7–36)NH$_2$, Val$^8$-GLP-1(7–37)OH, Val$^8$-GLP-1(7–36)NH$_2$, Lue$^8$-GLP-1(7–37)OH, Leu$^8$-GLP-1(7–36)NH$_2$, Ile$^8$-GLP-1(7–37)OH, Ile$^8$-GLP-1(7–36)NH$_2$, Ser$^8$-GLP-1(7–37)OH, Ser$^8$-GLP-1(7–36)NH$_2$, Thr$^8$-GLP-1(7–37)OH, Thr$^8$-GLP-1(7–36)NH$_2$, Val$^8$-Tyr$^{12}$-GLP-1(7–37)OH, Val$^8$-Tyr$^{12}$-GLP-1(7–36)NH$_2$, Val$^8$-Tyr$^{16}$-GLP-1(7–37)OH, Val$^8$-Tyr$^{16}$-GLP-1(7–36)NH$_2$, Val$^8$-Glu$^{22}$-GLP-1(7–37)OH, Val$^8$-Glu$^{22}$-GLP-1(7–36)NH$_2$, Gly$^8$-Glu$^{22}$-GLP-1(7–37)OH, Gly$^8$-Glu$^{22}$-GLP-1(7–36)NH$_2$, Val$^8$-Asp$^{22}$-GLP-1(7–37)OH, Val$^8$-Asp$^{22}$-GLP-1(7–36)NH$_2$, Gly$^8$-Asp$^{22}$-GLP-1(7–37)OH, Gly$^8$-Asp$^{22}$-GLP-1(7–36)NH$_2$, Val$^8$-Lys$^{22}$-GLP-1(7–37)OH, Val$^8$-Lys$^{22}$-GLP-1(7–36)NH$_2$, Gly$^8$-Lys$^{22}$-GLP-1(7–37)OH, Gly$^8$-Lys$^{22}$-GLP-1(7–36)NH$_2$, Leu$^8$-Glu$^{22}$-GLP-1(7–37)OH, Leu$^8$-Glu$^{22}$-GLP-1(7–36)NH$_2$, Ile$^8$-Glu$^{22}$-GLP-1(7–37)OH, Ile$^8$-Glu$^{22}$-GLP-1(7–36)NH$_2$, Leu$^8$-Asp$^{22}$-GLP-1(7–37)OH, Leu$^8$-Asp$^{22}$-GLP-1(7–36)NH$_2$, Ile$^8$-Asp$^{22}$-GLP-1(7–37)OH, Ile$^8$-Asp$^{22}$-GLP-1(7–36)NH$_2$, Leu$^8$-Lys$^{22}$-GLP-1(7–37)OH, Leu$^8$-Lys$^{22}$-GLP-1(7–36)NH$_2$, Ile$^8$-Lys$^{22}$-GLP-1(7–37)OH, Ile$^8$-Lys$^{22}$-GLP-1(7–36)NH$_2$, Ser$^8$-Glu$^{22}$-GLP-1(7–37)OH, Ser$^8$-Glu$^{22}$-GLP-1(7–36)NH$_2$, Thr$^8$-Glu$^{22}$-GLP-1(7–37)OH, Thr$^8$-Glu$^{22}$-GLP-1(7–36)NH$_2$, Ser$^8$-Asp$^{22}$-GLP-1(7–37)OH, Ser$^8$-Asp$^{22}$-GLP-1(7–36)NH$_2$, Thr$^8$-Asp$^{22}$-GLP-1(7–37)OH, Thr$^8$-Asp$^{22}$-GLP-1(7–36)NH$_2$, Ser$^8$-Lys$^{22}$-GLP-1(7–37)OH, Ser$^8$-Lys$^{22}$-GLP-1(7–36)NH$_2$, Thr$^8$-Lys$^{22}$-GLP-1(7–37)OH, Thr$^8$-Lys$^{22}$-GLP-1(7–36)NH$_2$, Glu$^{22}$-GLP-1(7–37)OH, Glu$^{22}$-GLP-1(7–36)NH$_2$, Asp$^{22}$-GLP-1(7–37)OH, Asp$^{22}$-GLP-1(7–36)NH$_2$, Lys$^{22}$-GLP-1(7–37)OH, Lys$^{22}$-GLP-1(7–36)NH$_2$, Val$^8$-Ala$^{27}$-GLP-1(7–37)OH, Val$^8$-Glu$^{22}$-Ala$^{27}$-GLP-1(7–37)OH, Val$^8$-Glu$^{30}$-GLP-1(7–37)OH, Val$^8$-Glu$^{30}$-GLP-1(7–36)NH$_2$, Gly$^8$-Glu$^{30}$-GLP-1(7–37)OH, Gly$^8$-Glu$^{30}$-GLP-1(7–36)NH$_2$, Leu$^8$-Glu$^{30}$-GLP-1(7–37)OH, Leu$^8$-Glu$^{30}$-GLP-1(7–36)NH$_2$, Ile$^8$-Glu$^{30}$-GLP-1(7–37)OH, Ile$^8$-Glu$^{30}$-GLP-1(7–36)NH$_2$, Ser$^8$-Glu$^{30}$-GLP-1(7–37)OH, Ser$^8$-Glu$^{30}$-GLP-1(7–36)NH$_2$, Thr$^8$-Glu$^{30}$-GLP-1(7–37)OH, Thr$^8$-Glu$^{30}$-GLP-1(7–36)NH$_2$, Val$^8$-His$^{37}$-GLP-1(7–37)OH, Val$^8$-His$^{37}$-GLP-1(7–36)NH$_2$, Gly$^8$-His$^{37}$-GLP-1(7–37)OH, Gly$^8$-His$^{37}$-GLP-1(7–36)NH$_2$, Leu$^8$-His$^{37}$-GLP-1(7–37)OH, Leu$^8$-His$^{37}$-GLP-1(7–36)NH$_2$, Ile$^9$-His$^{37}$-GLP-1(7–37)OH, Ile$^8$-His$^{37}$-GLP-1(7–36)NH$_2$, Ser$^8$-His$^{37}$-GLP-1(7–37)OH, Ser$^8$-His$^{37}$-GLP-1(7–36)NH$_2$, Thr$^8$-His$^{37}$-GLP-1(7–37)OH, Thr$^8$-His$^{37}$-GLP-1(7–36)NH$_2$.

The present invention also encompasses a GLP-1 compound comprising the amino acid sequence of formula II (SEQ ID NO:2)

Xaa$_7$-Xaa$_8$-Glu-Gly-Thr-Phe-Thr-Ser-Asp-Xaa$_{16}$-Ser-    Formula II (SEQ ID NO: 2)
Xaa$_{18}$-Tyr-Leu-Glu-Xaa$_{22}$-Gln-Ala-Xaa$_{25}$-Lys-Glu-Phe-
Ile-Ala-Trp-Leu-Xaa$_{33}$-Lys-Gly-Arg-Xaa$_{37}$ wherein:
Xaa$_7$ is: L-histidine, D-histidine, desamino-histidine, 2-amino-histidine, β-hydroxy-histidine, homohistidine, α-fluoromethyl-histidine, or (α-methyl-histidine);
Xaa$_8$ is: Gly, Ala, Val, Leu, Ile, Ser, or Thr;
Xaa$_{16}$ is: Val, Phe, Tyr, or Trp;
Xaa$_{18}$ is: Ser, Tyr, Trp, Phe, Lys, Ile, Leu, or Val;
Xaa$_{22}$ is: Gly, Glu, Asp, or Lys;
Xaa$_{25}$ is: Ala, Val, Ile, or Leu;
Xaa$_{33}$ is: Val or Ile; and
Xaa$_{37}$ is: Gly, NH$_2$, or is absent.

provided that the GLP-1 compound does not have the sequence of GLP-1(7–37)OH, GLP-1(7–36)-NH$_2$, Gly$^8$-GLP-1(7–37)OH, Gly$^8$-GLP-1(7–36)NH$_2$, Val$^8$-GLP-1(7–37)OH, Val$^8$-GLP-1(7–36)NH$_2$, Lue$^8$-GLP-1(7–37)OH, Leu$^8$-GLP-1(7–36)NH$_2$, Ile$^8$-GLP-1(7–37)OH, Ile$^8$-GLP-1(7–36)NH$_2$, Ser$^8$-GLP-1(7–37)OH, Ser$^8$-GLP-1(7–36)NH$_2$, Thr$^8$-GLP-1(7–37)OH, Thr$^8$-GLP-1(7–36)NH$_2$, Val$^8$-Tyr$^{16}$-GLP-1(7–37)OH, Val$^8$-Tyr$^{16}$-GLP-1(7–36)NH$_2$, Val$^8$-Glu$^{22}$-GLP-1(7–37)OH, Val$^8$-Glu$^{22}$-GLP-1(7–36)NH$_2$, Gly$^8$-Glu$^{22}$-GLP-1(7–37)OH, Gly$^8$-Glu$^{22}$-GLP-1(7–36)NH$_2$, Val$^8$-Asp$^{22}$-GLP-1(7–37)OH, Val$^8$-Asp$^{22}$-GLP-1(7–36)NH$_2$, Gly$^8$-Asp$^{22}$-GLP-1(7–37)OH, Gly$^8$-Asp$^{22}$-GLP-1(7–36)NH$_2$, Val$^8$-Lys$^{22}$-GLP-1(7–37)OH, Val$^8$-Lys$^{22}$-GLP-1(7–36)NH$_2$, Gly$^8$-Lys$^{22}$-GLP-1(7–37)OH, Gly$^8$-Lys$^{22}$-GLP-1(7–36)NH$_2$, Leu8-Glu$^{22}$-GLP-1(7–37)OH, Leu$^8$-Glu$^{22}$-GLP-1(7–36)NH$_2$, Ile$^8$-Glu$^{22}$-GLP-1(7–37)OH, Ile$^8$-Glu$^{22}$-GLP-1(7–36)NH$_2$, Leu$^8$-Asp$^{22}$-GLP-1(7–37)OH, Leu$^8$-Asp22 -GLP-1(7–36)NH$_2$, Ile$^8$-Asp$^{22}$-GLP-1(7–37)OH, Ile$^8$-Asp$^{22}$-GLP-1(7–36)NH$_2$, Leu$^8$-Lys$^{22}$-GLP-1(7–37)OH, Leu$^8$-Lys$^{22}$-GLP-1(7–36)NH$_2$, Ile$^8$-Lys$^{22}$-GLP-1(7–37)OH, Ile$^8$-Lys$^{22}$-GLP-1(7–36)NH$_2$, Ser$^8$-Glu$^{22}$-GLP-1(7–37)OH, Ser$^8$-Glu$^{22}$-GLP-1(7–36)NH$_2$, Thr$^8$-Glu$^{22}$-GLP-1(7–37)OH, Thr$^8$-Glu$^{22}$-GLP-1(7–36)NH$_2$, Ser$^8$-Asp$^{22}$-GLP-1(7–37)OH, Ser$^8$-Asp$^{22}$-GLP-1(7–36)NH$_2$, Thr$^8$-Asp$^{22}$-GLP-1(7–37)OH, Thr$^8$-Asp$^{22}$-GLP-1(7–36)NH$_2$, Ser$^8$-Lys$^{22}$-GLP-1(7–37)OH, Ser$^8$-Lys$^{22}$-GLP-1(7–36)NH$_2$, Thr$^8$-Lys$^{22}$-GLP-1(7–37)OH, Thr$^8$-Lys$^{22}$-GLP-1(7–36)NH$_2$, Glu$^{22}$-GLP-1(7–37)OH, Glu$^{22}$-GLP-1(7–36)NH$_2$, Asp$^{22}$-GLP-1(7–37)OH, Asp$^{22}$-GLP-1(7–36)NH$_2$, Lys$^{22}$-GLP-1(7–37)OH, Lys$^{22}$-GLP-1(7–36)NH$_2$, It is preferable that the GLP-1 compounds of formula I or II have 6 or fewer changes compared to the corresponding amino acids in native GLP-1(7–37)OH. More preferred analogs have 5 or fewer changes compared to the corresponding amino acids in native GLP-1(7–37)OH or have 4 or fewer changes compared to the corresponding amino acids in native GLP-1(7–37)OH or have 3 changes compared to the corresponding amino acids in native GLP-1(7–37)OH.

Some preferred GLP-1 compounds of formula I and II having multiple substitutions include GLP-1(7–37)OH wherein position 8 is valine or glycine, position 22 is glutamic acid, position 16 is tyrosine, leucine or tryptophan, position 18 is tyrosine, tryptophan, or isoleucine, position 25 is valine and position 33 is isoleucine. Other preferred GLP-1 compounds include the following: Val$^8$-Tyr$^{16}$-GLP-1(7–37)OH, Val$^8$-Tyr$^{12}$-Glu$^{22}$-GLP-1(7–37)OH, Val$^8$-Tyr$^{16}$-Phe$^{19}$-GLP-1(7–37)OH, Val$^8$-Tyr$^{16}$-Glu$^{22}$-GLP-1(7–37)OH, Val$^8$-Trp$^{16}$-Glu$^{22}$-GLP-1(7–37)OH, Val$^8$-Leu$^{16}$-Glu$^{22}$-GLP-1(7–37)OH, Val$^8$-Ile$^{16}$-Glu$^{22}$-GLP-1(7–37)OH, Val$^8$-Phe$^{16}$-Glu$^{22}$-GLP-1(7–37)OH, Val$^8$-Trp$^{18}$-Glu$^{22}$-GLP-1(7–37)OH, Val$^8$-Tyr$^{18}$-Glu$^{22}$-GLP-1(7–37)OH, Val$^8$-Phe$^{18}$-Glu$^{22}$-GLP-1(7–37)OH, and Val$^8$-Ile$^{18}$-Glu$^{22}$-GLP-1(7–37)OH.

Figure 2:
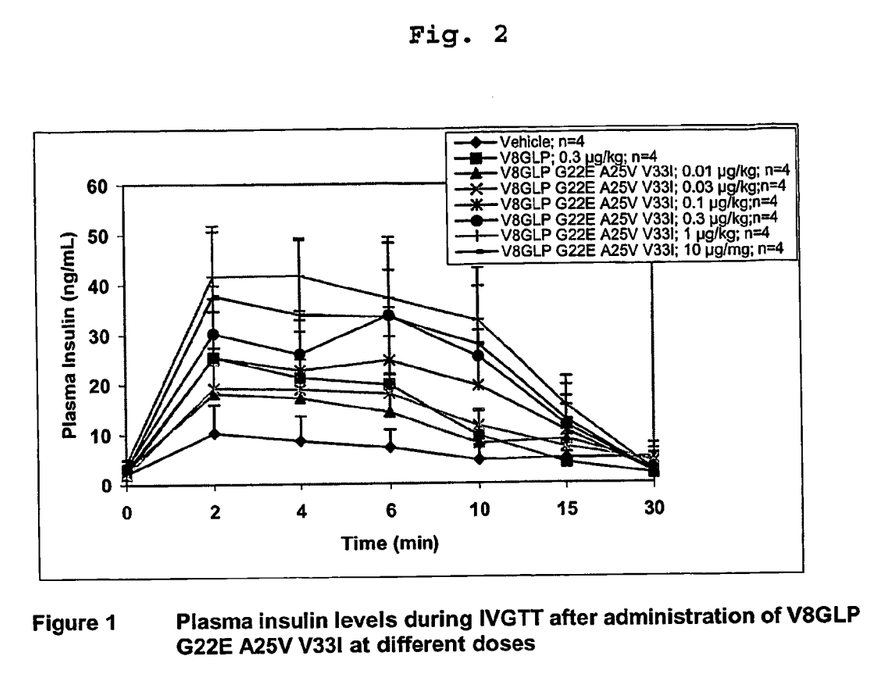
FIG. 2 graphs plasma insulin concentrations obtained at various time points after injection of increasing concentrations of Val⁸-Glu²²-Val²⁵-Ile³³-GLP-1 (7–37)OH in rats.
Figure 3:
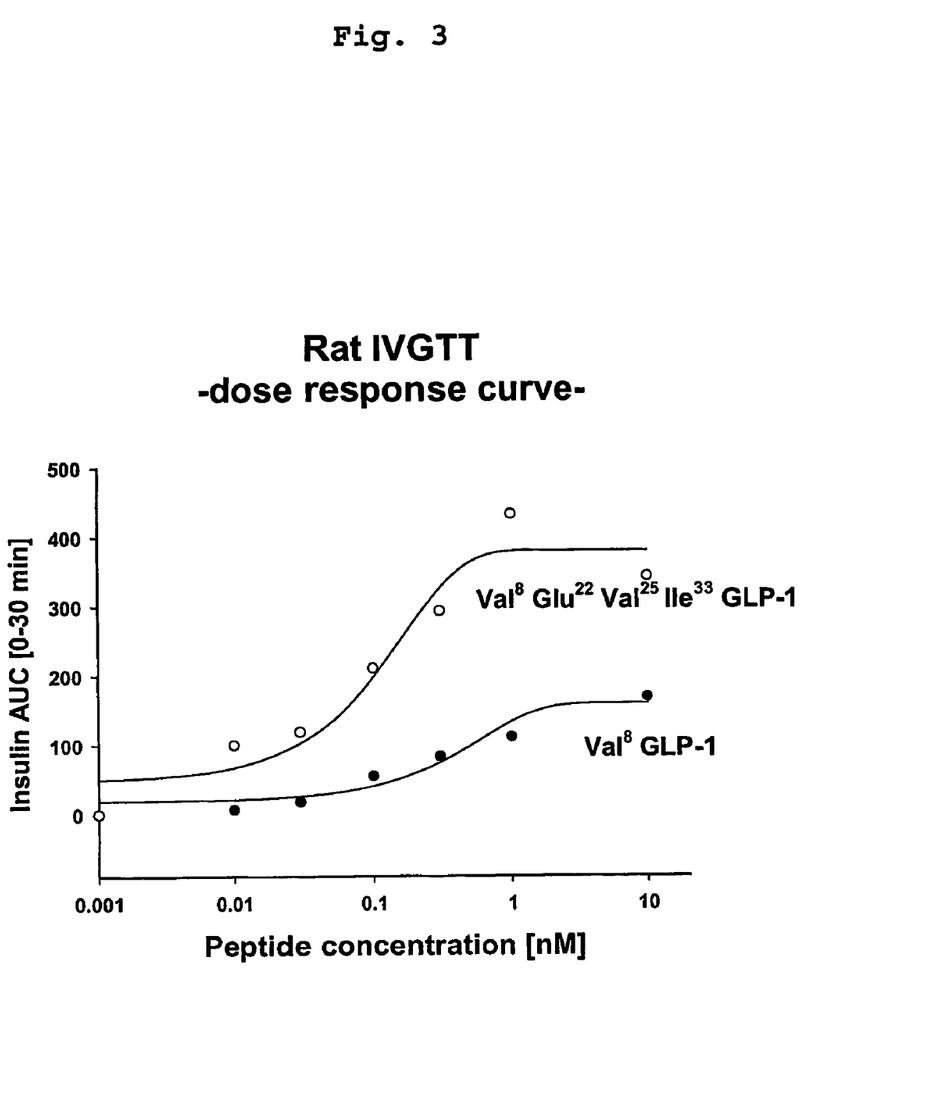
FIG. 3 graphs AUC values for plasma insulin for 0 to 30 min after injection of increasing concentrations of Val⁸-Glu²²-Val²⁵-Ile³³-GLP-1(7–37)OH in and Val⁸-GLP-1 (7–37)OH in rats.

Substitutions at the positions disclosed herein result in a GLP-1 compound with increased potency compared to the potency of Val$^8$-GLP-1(7–37)OH. The GLP-1 compounds of the present invention generally are between 3 and 6-fold more potent than Val$^8$-GLP-1(7–37)OH. For example, table I in example 4 provides a list of GLP-1 compounds with an in vitro potency compared to that obtained for Val$^8$-GLP-1 (7–37)OH. Preferably, the analogs are greater than 3-fold more potent than Val$^8$-GLP-1(7–37)OH. The in vitro potencies disclosed in table 1 are generally representative of in vivo potency relative to Val$^8$-GLP-1(7–37)OH. For example, FIGS. 2, 3, and 4 illustrate a higher in vivo potency for Val$^8$-Glu$^{22}$-Val$^{25}$-Ile$^{33}$-GLP-1(7–37)OH compared to Val$^8$-GLP-1(7–37)OH.

Furthermore, many of these more potent analogs have a reduced propensity to aggregate and thus, have increased stability. GLP-1 compounds can exist in at least two different forms. The first form is physiologically active and dissolves readily in aqueous solution at physiological pH (7.4). A second inactive form is readily produced when aqueous GLP-1 solutions are agitated, exposed to hydrophobic surfaces or have large air/water interfaces. The tendency to convert to the insoluble form considerably complicates the production of commercial quantities of active GLP-1 compounds. Thus, GLP-1 compounds that have a reduced propensity to aggregate in solution and are more potent than Val$^8$-GLP-1(7–37)OH are preferred. For example, the GLP-1 compounds Val$^8$-Glu$^{22}$-GLP-1(7–37) OH, Val$^8$-Glu$^{30}$-GLP-1(7–37)OH, and Val$^8$-His$^{37}$-GLP-1 (7–37)OH show a markedly decreased propensity to aggregate in solution compared to Val$^8$-GLP-1(7–37)OH (See example 3). Thus, preferred GLP-1 compounds of the present invention have either a glutamic acid at position 22, a glutamic acid at position 30, or a histidine at position 37 or combinations thereof in addition to substitutions at other positions such as 12, 16, 18, 19, 20, 25, 27, and 33.

As used herein, the term "GLP-1 compound" also includes pharmaceutically acceptable salts of the compounds described herein. A GLP-1 compound of this invention can possess a sufficiently acidic, a sufficiently basic, or both functional groups, and accordingly react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

Although the GLP-1 compounds of the present invention are particularly suited for oral administration, they can be delivered by nasal administration, inhalation or parenterally. Parenteral administration can include, for example, systemic administration, such as by intramuscular, intravenous, subcutaneous, or intraperitoneal injection. The GLP-1 compounds can be administered to the subject in conjunction with an acceptable pharmaceutical carrier, diluent or excipient as part of a pharmaceutical composition for treating the diseases discussed above. The pharmaceutical composition can be a solution or, if administered parenterally, a suspension of the GLP-1 compound or a suspension of the GLP-1 compound complexed with a divalent metal cation such as zinc. Suitable pharmaceutical carriers may contain inert ingredients which do not interact with the peptide or peptide derivative. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Some examples of suitable excipients include lactose, dextrose, sucrose, trehalose, sorbitol, and mannitol.

The GLP-1 compounds may be formulated for administration such that blood plasma levels are maintained in the efficacious range for extended time periods. Various means can be employed to achieve a protracted time action including, for example, the incorporation of GLP-1 compounds into suspended amorphous or crystalline particles wherein the GLP-1 compound is complexed with zinc and slowly solubilizes upon administration. GLP-1 particles that provide a protracted action are described in EP 926 159 by Hoffmann et al. and EP 619 322 by Danley et al. In addition, depot formulations wherein a bioadsorbable polymer is used to provide sustained release over time are also suitable for use in the present invention.

The main barrier to effective oral peptide drug delivery is poor bioavailability due to degradation of peptides by acids and enzymes, poor absorption through epithelial membranes, and transition of peptides to an insoluble form after exposure to the acidic pH environment in the digestive tract. This reduced bioavailability necessitates the use of GLP-1 compounds with increased potency. Oral delivery systems for peptides such as those encompassed by the present invention are known in the art. For example, GLP-1 compounds can be encapsulated using microspheres and then delivered orally. For example, GLP-1 compounds can be encapsulated into microspheres composed of a commercially available, biocompatible, biodegradable polymer, poly(lactide-co-glycolide)-COOH and olive oil as a filler. See Joseph et al. (2000) Diabetologia 43:1319–1328. Other types of microsphere technology is also available commercially such as Medisorb® and Prolease® biodegradable polymers from Alkermes. Medisorb® polymers can be produced with any of the lactide isomers. Lactide:glycolide ratios can be varied between 0:100 and 100:0 allowing for a broad range of polymer properties. This allows for the design of delivery systems and implantable devices with resorption times ranging from weeks to months. Emisphere has also published numerous articles discussing oral delivery technology for peptides and proteins. For example, see WO 9528838 by Leone-bay et al. which discloses specific carriers comprised of modified amino acids to facilitate absorption.

The GLP-1 compounds described herein can be used to treat subjects with a wide variety of diseases and conditions. GLP-1 compounds encompassed by the present invention exert their biological effects by acting at a receptor referred to as the "GLP-1 receptor" (see U.S. Pat. No. 5,670,360 to Thorrens). Subjects with diseases and/or conditions that respond favorably to GLP-1 receptor stimulation or to the adminstration of GLP-1 compounds can therefore be treated with the GLP-1 compounds of the present invention. These subjects are said to "be in need of treatment with GLP-1 compounds" or "in need of GLP-1 receptor stimulation".

Included are subjects with non-insulin dependent diabetes, insulin dependent diabetes, stroke (see WO 00/16797 by Efendic), myocardial infarction (see WO 98/08531 by Efendic), obesity (see WO 98/19698 by Efendic), catabolic changes after surgery (see U.S. Pat. No. 6,006,753 to Efendic), functional dyspepsia and irritable bowel syndrome (see WO 99/64060 by Efendic). Also included are subjects requiring prophylactic treatment with a GLP-1 compound, e.g., subjects at risk for developing non-insulin dependent diabetes (see WO 00/07617). Additional subjects include those with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

The GLP-1 compounds of the present invention can be used to normalize blood glucose levels, prevent pancreatic β-cell deterioration, induce β-cell proliferation, stimulate insulin gene transcription, up-regulate IDX-1/PDX-1 or other growth factors, improve β-cell function, activate dormant β-cells, differentiate cells into β-cells, stimulate β-cell replication, inhibit β-cell apoptosis, regulate body weight, and induce weight loss.

An "effective amount" of a GLP-1 compound is the quantity which results in a desired therapeutic and/or prophylactic effect without causing unacceptable side-effects when administered to a subject in need of GLP-1 receptor stimulation. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a GLP-1 compound for the treatment of diabetes is the quantity that would result in greater control of blood glucose concentration than in the absence of treatment, thereby resulting in a delay in the onset of diabetic complications such as retinopathy, neuropathy or kidney disease. An "effective amount" of a GLP-1 compound for the prevention of diabetes is the quantity that would delay, compared with the absence of treatment, the onset of elevated blood glucose levels that require treatment with anti-hypoglycaemic drugs such as sulfonyl ureas, thiazolidinediones, insulin and/or bisguanidines.

An "effective amount" of the GLP-1 compound administered to a subject will also depend on the type and severity of the disease and on the characteristics of the subject, such as general health, age, sex, body weight and tolerance to drugs. Typically, the GLP-1 compounds of the present invention will be administered such that plasma levels are within the range of about 5 picomoles/liter and about 200 picomoles/liter. Optimum plasma levels for $Val^8$-GLP-1 (7–37)OH were determined to be between 30 picomoles/liter and about 200 picomoles/liter. Because the GLP-1 compounds of the present invention are more potent than $Val^8$-GLP-1(7–37)OH, the optimum plasma levels will be lower. Generally, a GLP-1 compound that has an in vitro or in vivo potency that is 3-fold better than $Val^8$-GLP-1(7–37)OH will be administered such that plasma levels are 3-fold lower than the optimum levels determined for $Val^8$-GLP-1(7–37) OH.

A typical dose range for the GLP-1 compounds of the present invention will range from about 0.01 mg per day to about 1000 mg per day for an adult. Preferably, the dosage ranges from about 0.1 mg per day to about 100 mg per day, more preferably from about 1.0 mg/day to about 10 mg/day.

A "subject" is a mammal, preferably a human, but can also be an animal, e.g., companion animals (e.g., dogs, cats, and the like), farm animals (e.g., cows, sheep, pigs, horses, and the like) and laboratory animals (e.g., rats, mice, guinea pigs, and the like).

The GLP-1 compounds of the present invention can be prepared by using standard methods of solid-phase peptide synthesis techniques. Peptide synthesizers are commercially available from, for example, Applied Biosystems in Foster City, Calif. Reagents for solid phase synthesis are commercially available, for example, from Midwest Biotech (Fishers, Ind.). Solid phase peptide synthesizers can be used according to manufacturers instructions for blocking interfering groups, protecting the amino acid to be reacted, coupling, decoupling, and capping of unreacted amino acids.

Typically, an α-N-carbamoyl protected amino acid and the N-terminal amino acid on the growing peptide chain on a resin is coupled at room temperature in an inert solvent such as dimethylformamide, N-methylpyrrolidone or methylene chloride in the presence of coupling agents such as dicyclohexylcarbodiimide and 1-hydroxybenzotriazole and a base such as diisopropylethylamine. The α-N-carbamoyl protecting group is removed from the resulting peptide resin using a reagent such as trifluoroacetic acid or piperidine, and the coupling reaction repeated with the next desired N-protected amino acid to be added to the peptide chain. Suitable amine protecting groups are well known in the art and are described, for example, in Green and Wuts, "*Protecting Groups in Organic Synthesis*", John Wiley and Sons, 1991, the entire teachings of which are incorporated by reference. Examples include t-butyloxycarbonyl (tBoc) and fluorenylmethoxycarbonyl (Fmoc).

The peptides are also synthesized using standard automated solid-phase synthesis protocols using t-butoxycarbonyl- or fluorenylmethoxycarbonyl-alpha-amino acids with appropriate side-chain protection. After completion of synthesis, peptides are cleaved from the solid-phase support with simultaneous side-chain deprotection using standard hydrogen fluoride methods. Crude peptides are then further purified using Reversed-Phase Chromatography on Vydac C18 columns using acetonitrile gradients in 0.1% trifluoroacetic acid (TFA). To remove acetonitrile, peptides are lyophilized from a solution containing 0.1% TFA, acetonitrile and water. Purity can be verified by analytical reversed phase chromatography. Identity of peptides can be verified by mass spectrometry. Peptides can be solubilized in aqueous buffers at neutral pH.

The invention is illustrated by the following examples which are not intended to be limiting in any way.

EXAMPLE 1

Preparation of the GLP-1 Compounds of the Present Invention by Solid Phase t-Boc Chemistry Approximately 0.5–0.6 grams (0.38–0.45 mmole) Boc Gly-PAM resin was placed in a standard 60 ml reaction vessel and double couplings were run on an Applied Biosytems ABI430A peptide synthesizer. The following sidechain protected amino acids (2 mmole cartridges of Boc amino acids) were obtained from Midwest Biotech (Fishers, Ind.) and used in the synthesis:

Arg-Tosyl (TOS), Asp-δ-cyclohexyl ester(CHXL), Glu-δ-cycohexyl ester (CHXL), His-benzyloxymethyl(BOM), Lys-2-chlorobenzyloxycarbonyl (2Cl-Z), Met-sulfoxide (O), Ser-O-benzyl ether (OBzl), Thr-O-benzyl ether (OBzl), Trp-formyl (CHO) and Tyr-2-bromobenzyloxycarbonyl (2Br-Z) and Boc Gly PAM resin. Trifluoroacetic acid (TFA), di-isopropylethylamine (DIEA), 0.5 M hydroxybenzotriazole (HOBt) in DMF and 0.5 M dicyclohexylcarbodiimide (DCC) in dichloromethane were purchased from PE-Applied Biosystems (Foster City, Calif.). Dimethylformamide (DMF-Burdick and Jackson) and dichloromethane (DCM-Mallinkrodt) were purchased from Mays Chemical Co. (Indianapolis, Ind.).

Standard double couplings were run using either symmetric anhydride or HOBt esters, both formed using DCC. A second set of double couplings (without TFA deprotection) were run at Trp31, Thr13 and Thr11. At the completion of the syntheses, the N-terminal Boc group was removed and the peptidyl resins treated with 20% piperidine in DMF to deformylate the Trp side chain. After washing with DCM, the resins were transferred to a TEFLON reaction vessel and dried in vacuo.

For analogs containing Met, an on-the-resin reduction was done using TFA/10% dimethyl sulfide (DMS)/2% concentrated HCl. Cleavages were done by attaching the reaction vessels to a HF (hydrofluoric acid) apparatus (Penninsula Laboratories). 1 ml m-cresol per gram/resin was added and 10 ml HF (purchased from AGA, Indianapolis, Ind.) was condensed into the pre-cooled vessel. 1 ml DMS per gram resin was added when methionine was present. The reactions were stirred one hour in an ice bath and the HF removed in vacuo. The residues were suspended in ethyl ether and the solids were filtered and washed with ether. Each peptide was extracted into aqueous acetic acid and either freeze dried or loaded directly onto a reverse-phase column.

Purifications were run on a 2.2×25 cm VYDAC C18 column in buffer A (0.1% Trifluoroacteic acid in water, B: 0.1% TFA in acetonitrile). A gradient of 20% to 90% B was run on an HPLC (Waters) over 120 minutes at 10 ml/minute while monitoring the UV at 280 nm (4.0 A) and collecting one minute fractions. Appropriate fractions were combined, frozen and lyophilized. Dried products were analyzed by HPLC (0.46×15 cm METASIL AQ C18) and MALDI mass spectrometry.

EXAMPLE 2

Preparation of the GLP-1 Compounds of the Present Invention by Solid Phase F-Moc Chemistry Approximately 114 mg (50 mMole) FMOC Gly WANG resin (purchased from NovaBiochem, LaJolla, Calif.) was placed in each programmed well of the 96well reaction block and double couplings were run on an Advanced ChemTech 396 peptide synthesizer. Analogs with a C-terminal amide were prepared using 75 mg (50 µmole) Rink Amide AM resin (NovaBiochem, LaJolla, Calif.).

The following FMOC amino acids were purchased from Advanced ChemTech (Louisville, Ky.), NovaBiochem (La Jolla, Calif.), and Midwest BioTech (Fishers, Ind.): Arg-2,2,4,6,7-pentamethyldihydrobenzofuran-5-sulfonyl (Pbf), Asn-trityl (Trt), Asp-β-t-Butyl ester (tBu), Glu-δ-t-butyl ester (tBu), Gln-trityl (Trt), His-trityl (Trt), Lys-t-butyloxycarbonyl (Boc), Ser-t-butyl ether (OtBu), Thr-t-butyl ether (OtBu), Trp-t-butyloxycarbonyl (Boc), Tyr-t-butyl ether (OtBu).

Solvents dimethylformamide (DMF-Burdick and Jackson), N-methyl pyrrolidone (NMP-Burdick and Jackson), dichloromethane (DCM-Mallinkrodt) were purchased from Mays Chemical Co. (Indianapolis, Ind.).

Hydroxybenzotrizole (HOBt), di-isopropylcarbodiimde (DIC), di-isopropylethylamine (DIEA), and piperidine (Pip) were purchased from Aldrich Chemical Co (Milwaukee, Wis.).

All amino acids were dissolved in 0.45 M HOBt in NMP and 50 minutes DIC/HOBt activated couplings were run after 20 minutes deprotection using 20% Pip/DMF. Each resin was washed with DMF after deprotections and couplings. After the last coupling and deprotection, the peptidyl resins were washed with DCM and dried in vacuo in the reaction block.

With the reaction/cleavage block assembly in place, 2 ml Reagent K was added to each well and the cleavage reaction mixed for 2 hours [Reagent K=0.75 gm phenol, 0.5 ml thioanisole, 0.25 ml ethanedithiol, 0.5 ml water per 10 ml trifluoroacetic acid (TFA), all purchased from Aldrich Chemical Co., Milwaukee, Wis.]. The TFA filtrates were added to 40 ml ethyl ether and the precipitants centrifuged 2 minutes at 2000 rpm. The supernatants were decanted, the pellets re-suspended in 40 ml ether, re-centrifuged, re-decanted, dried under nitrogen and then in vacuo.

0.3–0.6 mg of each product was dissolved in 1 ml 0.1% TFA/acetonitrile(ACN) and 20 ul was analyzed on HPLC [0.46×15 cm METASIL AQ C18, 1 ml/min, 45° C., 214 nM (0.2 A), A=0.1% TFA, B=0.1% TFA/50% ACN. Gradient=50% B to 90% B over 30 minutes].

Purifications were run on a 2.2×25 cm VYDAC C18 column in buffer A (0.1% trifluoroacteic acid in water, B: 0.1% TFA in acetonitrile). A gradient of 20% to 90% B was run on an HPLC (Waters) over 120 minutes at 10 ml/minute while monitoring the UV at 280 nm (4.0 A) and collecting 1 minute fractions. Appropriate fractions were combined, frozen and lyophilized. Dried products were analyzed by HPLC (0.46×15 cm METASIL AQ C18) and MALDI mass spectrometry.

EXAMPLE 3

GLP Aggregation Assay

GLP peptides of this invention were analyzed with respect to their potential to aggregate in solution. In general, peptides in solution were stirred at elevated temperature in a suitable buffer while recording turbidity at 350 nm as a function of time. Time to the onset of aggregation was measured to quantify the potential of a given GLP molecule to aggregate under these stressed conditions.

Protocol:

A GLP-1 compound was first dissolved under alkaline conditions (pH 10.5) for 30 minutes to dissolve any pre-aggregated material. The solution was then adjusted to pH 7.4 and filtered. Specifically, 4 mg of a lyophilized GLP-1 compound was dissolved in 3 ml of 10 mM phosphate/10 mM citrate. The pH was adjusted to 10.0–10.5 and held for 30 minutes. The solution was adjusted with HCl to pH 7.4 and filtered through a suitable filter, for example a Millex GV syringe filter (Millipore Corporation, Bedford, Mass.). This solution was then diluted to a final sample containing 0.3 mg/mL protein in 10 mM citrate, 10 mM phosphate, 150 mM NaCl, and adjusted to pH 7.4 to 7.5. The sample was incubated at 37° C. in a quartz cuvette. Every five minutes the turbidity of the solution was measured at 350 nm on an AVIV Model 14DS UV-VIS spectrophotometer (Lakewood, N.J.). For 30 seconds prior to and during the measurement the solution was stirred using a magnetic stir bar from Starna Cells, Inc. (Atascadero, Calif.). An increase in OD at 350 nm indicates aggregation of the GLP-peptide. The time to aggregation was approximated by the intersection of linear fits to the pre-growth and growth phase according to method of Drake (Arvinte T, Cudd A, and Drake A F. (1993) *J. Bio. Chem.* 268, 6415–6422).

The cuvette was cleaned between experiments with a caustic soap solution (e.g., Contrad-70).

The results for a number of GLP-1 compounds of the present invention are reported in Table 1 as the time in hours required for the compound to aggregate. As can be seen, the compounds of the present invention show greatly increased aggregation times over GLP-1 compounds known in the prior art.

The GLP-1 compound $Val^8$-$Glu^{22}$-GLP-1(7–37)OH had an aggregation time of approximately 72 hours at 30° C. compared to an aggregation time of less than 1 hour for $Val^8$-GLP-1(7–37)OH at 30° C. The GLP-1 compound $Val^8$-$Glu^{30}$-GLP-1(7–37)OH had an aggregation time of approximately 30 hours and the GLP-1 compound $Val^8$-$His^{37}$-GLP-1(7–37)OH had an aggregation time greater than 40 hours at 30° C.

EXAMPLE 4

GLP-1 Receptor Activation with the GLP-1 Compounds of the Present Invention

The ability of the GLP-1 compounds of the present invention to activate the GLP-1 receptor was assessed using in vitro assays such as those described in EP 619,322 to Gelfand, et al., and U.S. Pat. No. 5,120,712, respectively. The entire teachings of these references are incorporated herein by reference. The activity of these compounds relative to the activity of $Val^8$-GLP-1(7–37)OH is reported in Table 1.

TABLE 1

| Compound | GLP-1 receptor activation relative to $Val^8$-GLP-1(7-37)OH |
|---|---|
| GLP-1(7-37)OH | 2.1 |
| $Val^8$-GLP-1(7-37)OH | 1.0 |
| $Gly^8$-GLP-1(7-37)OH | 1.7 |
| $Val^8$-$Tyr^{12}$-GLP-1(7-37)OH | 1.7 |
| $Val^8$-$Tyr^{12}$-GLP-1(7-36)NH$_2$ | 1.1 |
| $Val^8$-$Trp^{12}$-GLP-1(7-37)OH | 1.1 |
| $Val^8$-$Leu^{16}$-GLP-1(7-37)OH | 1.1 |
| $Val^8$-$Tyr^{16}$-GLP-1(7-37)OH | 2.5 |
| $Gly^8$-$Glu^{22}$-GLP-1(7-37)OH | 2.2 |
| $Val^8$-$Leu^{25}$-GLP-1(7-37)OH | 0.5 |
| $Val^8$-$Glu^{30}$-GLP-1(7-37)OH | 0.7 |
| $Val^8$-$His^{37}$-GLP-1(7-37)OH | 1.2 |

TABLE 1-continued

| Compound | GLP-1 receptor activation relative to $Val^8$-GLP-1(7-37)OH |
|---|---|
| $Val^8$-$Tyr^{12}$-$Tyr^{16}$-GLP-1(7-37)OH | 1.5 |
| $Val^8$-$Trp^{12}$-$Glu^{22}$-GLP-1(7-37)OH | 1.7 |
| $Val^8$-$Tyr^{12}$-$Glu^{22}$-GLP-1(7-37)OH | 2.7 |
| $Val^8$-$Tyr^{16}$-$Phe^{19}$-GLP-1(7-37)OH | 2.8 |
| $Val^8$-$Tyr^{16}$-$Glu^{22}$-GLP-1(7-37)OH | 3.6, 3.8 |
| $Val^8$-$Tyr^{16}$-$Glu^{22}$-GLP-1(7-37)OH | 4.9, 4.6 |
| $Val^8$-$Leu^{16}$-$Glu^{22}$-GLP-1(7-37)OH | 4.3 |
| $Val^8$-$Ile^{16}$-$Glu^{22}$-GLP-1(7-37)OH | 3.3 |
| $Val^8$-$Phe^{16}$-$Glu^{22}$-GLP-1(7-37)OH | 2.3 |
| $Val^8$-$Trp^{18}$-$Glu^{22}$-GLP-1(7-37)OH | 3.2, 6.6 |
| $Val^8$-$Tyr^{18}$-$Glu^{22}$-GLP-1(7-37)OH | 5.1, 5.9 |
| $Val^8$-$Phe^{18}$-$Glu^{22}$-GLP-1(7-37)OH | 2.0 |
| $Val^8$-$Ile^{18}$-$Glu^{22}$-GLP-1(7-37)OH | 4.0 |
| $Val^8$-$Lys^{18}$-$Glu^{22}$-GLP-1(7-37)OH | 2.5 |
| $Val^8$-$Trp^{19}$-$Glu^{22}$-GLP-1(7-37)OH | 3.2 |
| $Val^8$-$Phe^{19}$-$Glu^{22}$-GLP-1(7-37)OH | 1.5 |
| $Val^8$-$Phe^{20}$-$Glu^{22}$-GLP-1(7-37)OH | 2.7 |
| $Val^8$-$Glu^{22}$-$Leu^{25}$-GLP-1(7-37)OH | 2.8 |
| $Val^8$-$Glu^{22}$-$Ile^{25}$-GLP-1(7-37)OH | 3.1 |
| $Val^8$-$Glu^{22}$-$Val^{25}$-GLP-1(7-37)OH | 4.7, 2.9 |
| $Val^8$-$Glu^{22}$-$Ile^{27}$-GLP-1(7-37)OH | 2.0 |
| $Val^8$-$Glu^{22}$-$Ala^{27}$-GLP-1(7-37)OH | 2.2 |
| $Val^8$-$Glu^{22}$-$Ile^{33}$-GLP-1(7-37)OH | 4.7, 3.8, 3.4 |
| $Val^8$-$Glu^{22}$-$His^{37}$-GLP-1(7-37)OH | 4.7 |
| $Val^8$-$Asp^9$-$Ile^{11}$-$Tyr^{16}$-$Glu^{22}$-GLP-1(7-37)OH | 4.3 |
| $Val^8$-$Tyr^{16}$-$Trp^{19}$-$Glu^{22}$-GLP-1(7-37)OH | 3.5 |
| $Val^8$-$Trp^{16}$-$Glu^{22}$-$Val^{25}$-$Ile^{33}$-GLP-1(7-37)OH | 5.0 |
| $Val^8$-$Trp^{16}$-$Glu^{22}$-$Ile^{33}$-GLP-1(7-37)OH | 4.1 |
| $Val^8$-$Glu^{22}$-$Val^{25}$-$Ile^{33}$-GLP-1(7-37)OH | 4.9, 5.8, 6.7 |
| $Val^8$-$Trp^{16}$-$Glu^{22}$-$Val^{25}$-GLP-1(7-37)OH | 4.4 |

EXAMPLE 5

Intravenous Glucose Tolerance Test (IVGTT) in Rats

Figure 1:
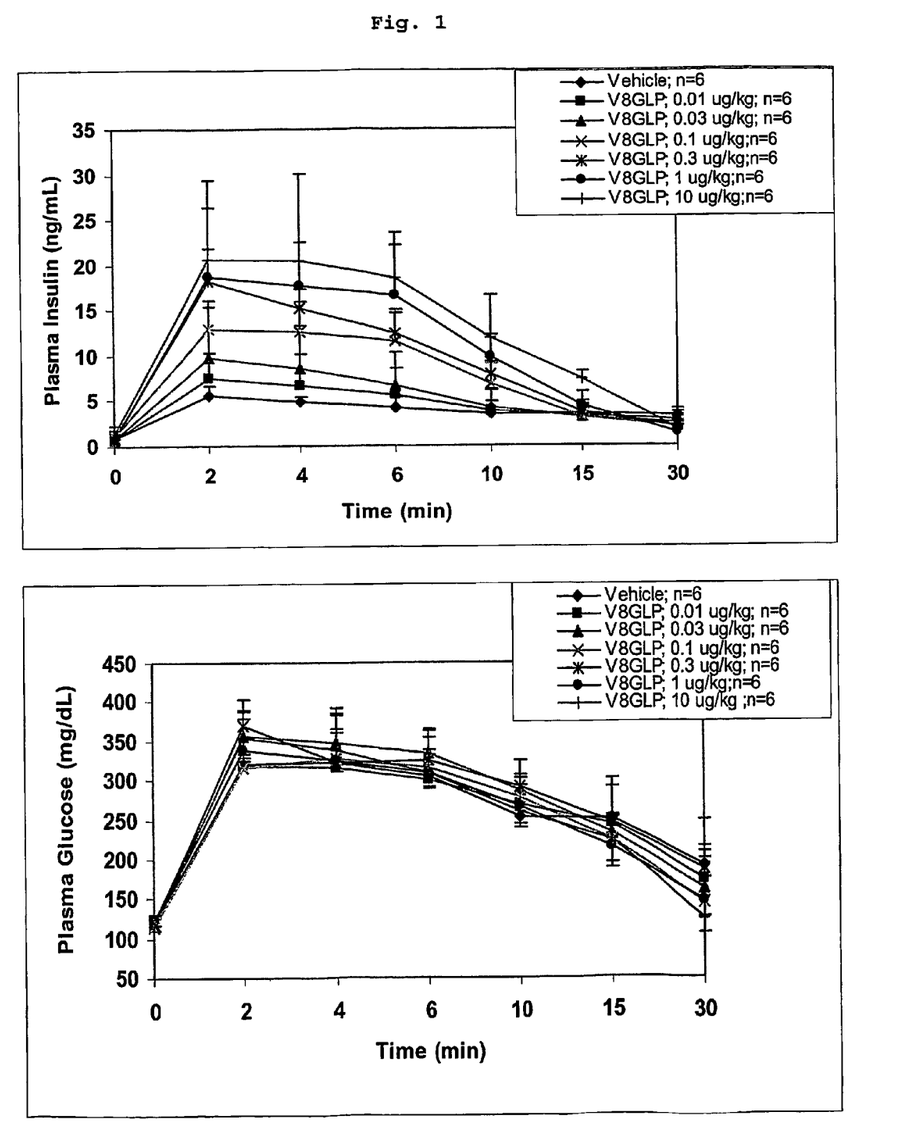

A double cannulation procedure was performed on fasting wistar male rats to facilitate injection of solutions and withdrawal of blood. Rats were injected through the jugular cannula with a bolus of 10% glucose solution followed by a solution containing a specific amount of a GLP-1 compound. Rats were injected with 0.01, 0.03, 0.1, 0.3, 1, and 10 μg/kg of GLP-1 compound. Blood was collected through the carotid cannula 2, 4, 6, 10, and 30 minutes following the injection of GLP-1 compound and analyzed. Plasma insulin and plasma glucose levels were measured in each sample. Average insulin and glucose levels are illustrated in FIGS. 1, 2, and 3.

What is claimed is:

1. A GLP-1 compound comprising the amino acid sequence: His-Val-Glu-Gly-Thr-Phe-Thr-Ser-Asp-Val-Ser-Ser-Tyr-Leu-Glu-Glu-Gln-Ala-Ala-Lys-Glu-Phe-Ile-Ala-Trp-Leu-Ile-Lys-Gly-Arg-Gly-OH.

2. A method of stimulating the GLP-1 receptor in a subject in need of such stimulation, said method comprising the step of administering to the subject an effective amount of the GLP-1 compound of claim 1.

3. The method of claim 1 wherein the subject is being treated for non-insulin dependent diabetes.

4. The method of claim 1 wherein the subject is being treated prophylactically for non-insulin dependent diabetes.

5. The method of claim 1 wherein the subject is being treated for obesity, stroke, myocardial infarction, stroke or irritable bowel syndrome.

* * * * *

SEQUENCE LISTING

<160> NUMBER OF SEQ ID NOS: 3

<210> SEQ ID NO 1
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, alpha-fluoromethyl-histidine, or
      alpha-methyl-histidine;
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile,
      Ser, or Thr;
<220> FEATURE:
<221> NAME/KEY: MISC_FEATURE
<222> LOCATION: (6)..(6)
<223> OTHER INFORMATION: Xaa at position 6 is Phe, Trp, or Tyr;
<220> FEATURE:
<221> NAME/KEY: MISC_FEATURE
<222> LOCATION: (10)..(10)
<223> OTHER INFORMATION: Xaa at position 10 is Val, Trp, Ile, Leu, Phe,
      or Tyr;
<220> FEATURE:
<221> NAME/KEY: MISC_FEATURE
<222> LOCATION: (12)..(12)
<223> OTHER INFORMATION: Xaa at position 12 is Ser, Trp, Tyr, Phe, Lys,
      Ile, Leu, or Val;
<220> FEATURE:
<221> NAME/KEY: MISC_FEATURE
<222> LOCATION: (13)..(13)
<223> OTHER INFORMATION: Xaa at position 13 is Tyr, Trp, or Phe;
<220> FEATURE:
<221> NAME/KEY: MISC_FEATURE
<222> LOCATION: (14)..(14)
<223> OTHER INFORMATION: Xaa at position 14 is Leu, Phe, Tyr, or Trp;
<220> FEATURE:
<221> NAME/KEY: MISC_FEATURE
<222> LOCATION: (16)..(16)
<223> OTHER INFORMATION: Xaa at position 16 is Gly, Glu, Asp, or Lys;
<220> FEATURE:
<221> NAME/KEY: MISC_FEATURE
<222> LOCATION: (19)..(19)
<223> OTHER INFORMATION: Xaa at position 19 is Ala, Val, Ile, or Leu;
<220> FEATURE:
<221> NAME/KEY: MISC_FEATURE
<222> LOCATION: (21)..(21)
<223> OTHER INFORMATION: Xaa at position 21 is Glu, Ile, or Ala;
<220> FEATURE:
<221> NAME/KEY: MISC_FEATURE
<222> LOCATION: (24)..(24)
<223> OTHER INFORMATION: Xaa at position 24 is Ala or Glu;
<220> FEATURE:
<221> NAME/KEY: MISC_FEATURE
<222> LOCATION: (27)..(27)
<223> OTHER INFORMATION: Xaa at position 27 is Val, or Ile; and
<220> FEATURE:
<221> NAME/KEY: MISC_FEATURE
<222> LOCATION: (31)..(31)
<223> OTHER INFORMATION: Xaa at position 31 is Gly, His, or is absent.
<220> FEATURE:
<221> NAME/KEY: MOD_RES
<222> LOCATION: (30)..(30)
<223> OTHER INFORMATION: Arg at position 30 may be amidated.

<400> SEQUENCE: 1

Xaa Xaa Glu Gly Thr Xaa Thr Ser Asp Xaa Ser Xaa Xaa Xaa Glu Xaa
1               5                   10                  15

```
Gln Ala Xaa Lys Xaa Phe Ile Xaa Trp Leu Xaa Lys Gly Arg Xaa
            20                  25                  30
```

<210> SEQ ID NO 2
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, alpha-fluoromethyl-histidine, or
      alpha-methyl-histidine;
<220> FEATURE:
<221> NAME/KEY: MISC_FEATURE
<222> LOCATION: (2)..(2)
<223> OTHER INFORMATION: Xaa at position 2 is Gly, Ala, Val, Leu, Ile,
      Ser, or Thr;
<220> FEATURE:
<221> NAME/KEY: MISC_FEATURE
<222> LOCATION: (10)..(10)
<223> OTHER INFORMATION: Xaa at position 10 is Val, Phe, Tyr, or Trp;
<220> FEATURE:
<221> NAME/KEY: MISC_FEATURE
<222> LOCATION: (12)..(12)
<223> OTHER INFORMATION: Xaa at position 12 is Ser, Tyr, Trp, Phe, Lys,
      Ile, Leu, or Val;
<220> FEATURE:
<221> NAME/KEY: MISC_FEATURE
<222> LOCATION: (16)..(16)
<223> OTHER INFORMATION: Xaa at position 16 is Gly, Glu, Asp, or Lys;
<220> FEATURE:
<221> NAME/KEY: MISC_FEATURE
<222> LOCATION: (19)..(19)
<223> OTHER INFORMATION: Xaa at position 19 is Ala, Val, Ile, or Leu;
<220> FEATURE:
<221> NAME/KEY: MISC_FEATURE
<222> LOCATION: (27)..(27)
<223> OTHER INFORMATION: Xaa at position 27 is Val or Ile; and
<220> FEATURE:
<221> NAME/KEY: MISC_FEATURE
<222> LOCATION: (31)..(31)
<223> OTHER INFORMATION: Xaa at position 31 is Gly or is absent.
<220> FEATURE:
<221> NAME/KEY: MOD_RES
<222> LOCATION: (30)..(30)
<223> OTHER INFORMATION: Arg at position 30 may be amidated.

<400> SEQUENCE: 2

```
Xaa Xaa Glu Gly Thr Phe Thr Ser Asp Xaa Ser Xaa Tyr Leu Glu Xaa
1               5                   10                  15

Gln Ala Xaa Lys Glu Phe Ile Ala Trp Leu Xaa Lys Gly Arg Xaa
            20                  25                  30
```

<210> SEQ ID NO 3
<211> LENGTH: 31
<212> TYPE: PRT
<213> ORGANISM: Homo sapiens

<400> SEQUENCE: 3

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```